United States Patent [19]

Spaulding

[11] Patent Number: 5,304,200
[45] Date of Patent: Apr. 19, 1994

[54] WELDED RADIALLY EXPANDABLE ENDOPROSTHESIS AND THE LIKE

[75] Inventor: Ronald N. Spaulding, Miami, Fla.

[73] Assignee: Cordis Corporation, Miami, Fla.

[21] Appl. No.: 4,179

[22] Filed: Jan. 13, 1993

Related U.S. Application Data

[63] Continuation of Ser. No. 706,964, May 29, 1991, abandoned.

[51] Int. Cl.⁵ .............................................. A61F 2/06
[52] U.S. Cl. .................................... 606/198; 606/195; 623/1; 623/901
[58] Field of Search ................... 604/8, 104, 281–282, 604/96–103; 606/108, 192–194, 198, 195; 623/1, 11–12, 901

[56] References Cited

U.S. PATENT DOCUMENTS

| | | | |
|---|---|---|---|
| 3,657,744 | 4/1972 | Ersek | 623/11 |
| 4,078,167 | 3/1978 | Banas et al. | 219/121.63 |
| 4,127,761 | 11/1978 | Pauley et al. | 219/121.64 |
| 4,553,545 | 11/1985 | Maass et al. | 606/198 |
| 4,580,568 | 4/1986 | Gianturco | 606/198 |
| 4,649,922 | 3/1987 | Wiktor | 606/194 |
| 4,655,776 | 4/1987 | Lesinski | 623/10 |
| 4,658,110 | 4/1987 | Miller et al. | 219/121.64 |
| 4,733,665 | 3/1988 | Palmaz | 604/96 |
| 4,738,389 | 4/1988 | Moshier et al. | 228/198 |
| 4,739,762 | 4/1988 | Palmaz | 604/96 |
| 4,762,128 | 8/1988 | Rosenbluth | 604/96 |
| 4,776,337 | 10/1988 | Palmaz | 606/194 |
| 4,800,882 | 1/1989 | Gianturco | 606/194 |
| 4,830,003 | 5/1989 | Wolff et al. | 606/191 |
| 4,851,009 | 7/1989 | Pinchuck | 623/1 |
| 4,856,516 | 8/1989 | Hillstead | 604/96 |
| 4,886,062 | 12/1989 | Wiktor | 623/1 |
| 4,913,141 | 4/1990 | Hillstead | 606/194 |
| 4,922,905 | 5/1990 | Strecker | 623/12 |
| 4,969,458 | 11/1990 | Wiktor | 606/194 |
| 4,994,071 | 2/1991 | MacGregor | 606/192 |
| 5,015,253 | 5/1991 | MacGregor | 623/1 |
| 5,019,085 | 5/1991 | Hillstead | 606/198 |
| 5,019,090 | 5/1991 | Pinchuk | 606/194 |
| 5,035,706 | 7/1991 | Giantureo et al. | 606/198 |
| 5,037,427 | 8/1991 | Harada et al. | 604/96 |
| 5,041,126 | 8/1991 | Gianturco | 623/1 |

FOREIGN PATENT DOCUMENTS 0357003 3/1990 European Pat. Off. ............ 623/901

OTHER PUBLICATIONS

Van Nostrand's Scientific Encyclopedia (6th ed), Van Nostrand Reinhold Co., New York, 1983.

Primary Examiner—C. Fred Rosenbaum
Assistant Examiner—Mark Bockelman
Attorney, Agent, or Firm—Lockwood, Alex, FitzGibbon & Cummings

[57] ABSTRACT

Radially expandable endoprostheses or stents are provided, as well as their method of manufacture. These stents include a plurality of adjacent generally circumferential sections that are substantially axially positioned with respect to each other. Included are generally circumferentially disposed expandable segments that impart circumferential and radial expandability to the stents. The terminal portions of the end circumferential sections are welded directly to a portion of a generally adjacent circumferential section, and the welding preferably is carried out within an inert gas environment in a manner that minimizes crack formation at the weld locations.

12 Claims, 4 Drawing Sheets

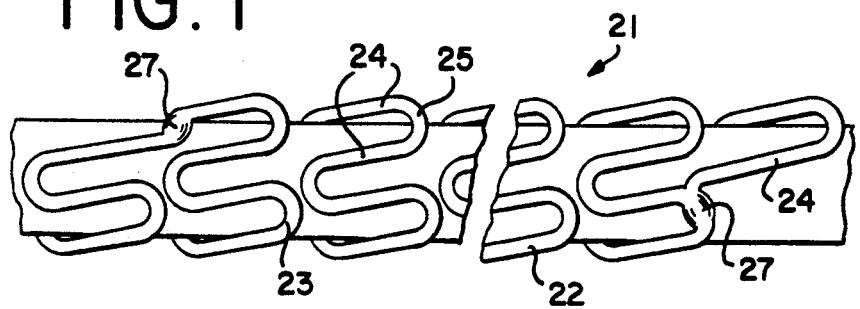
FIG. 1
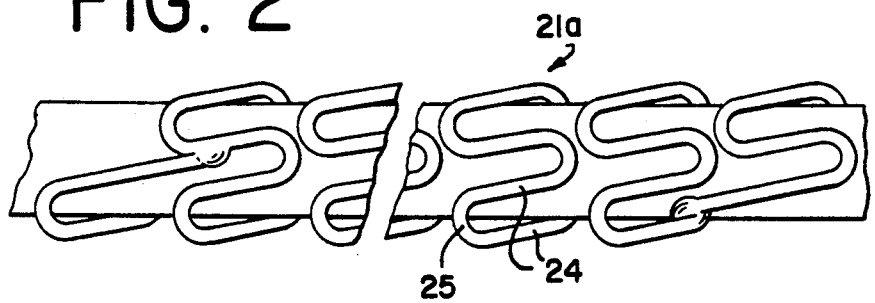
FIG. 2
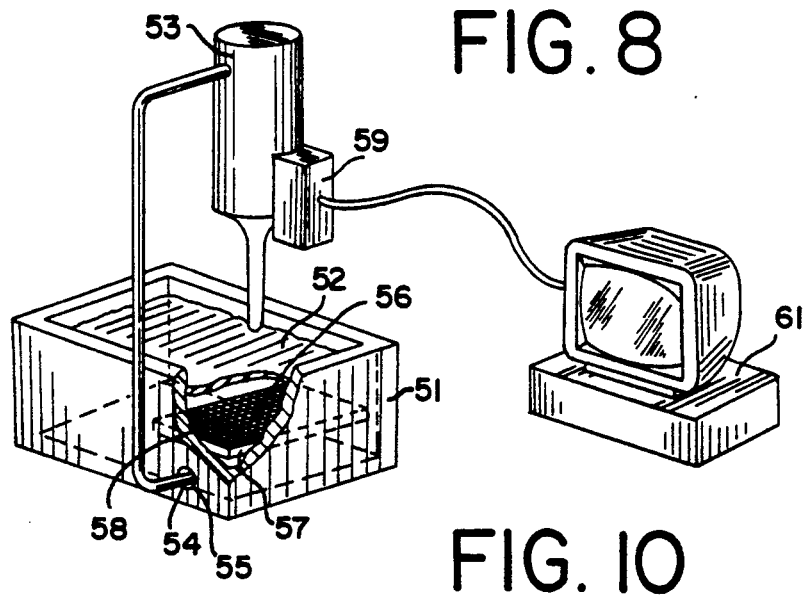
FIG. 8
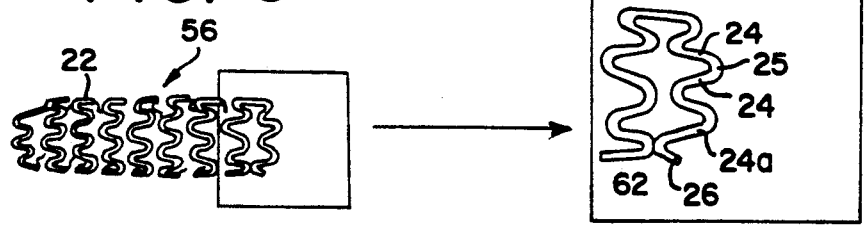
FIG. 9
FIG. 10

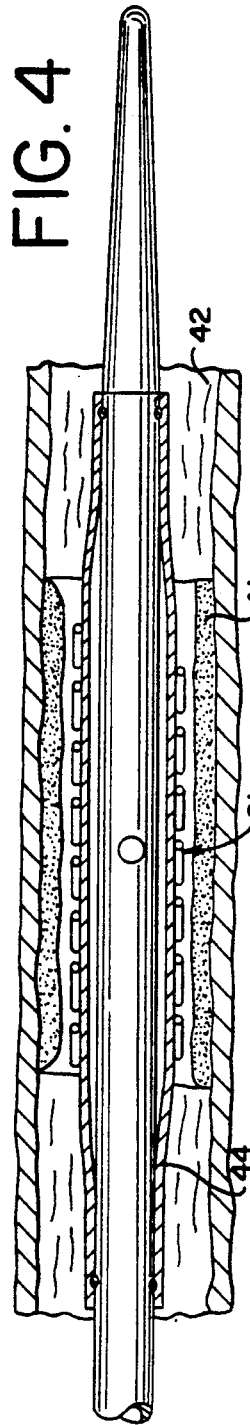
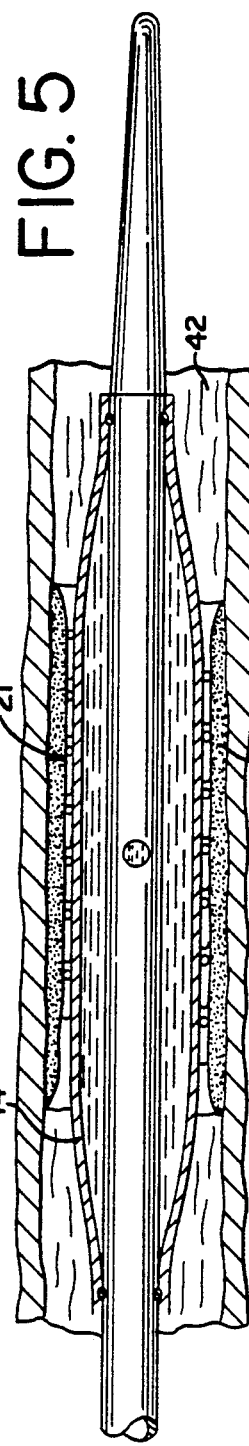
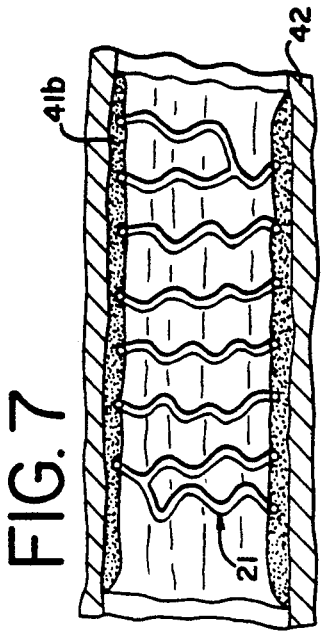
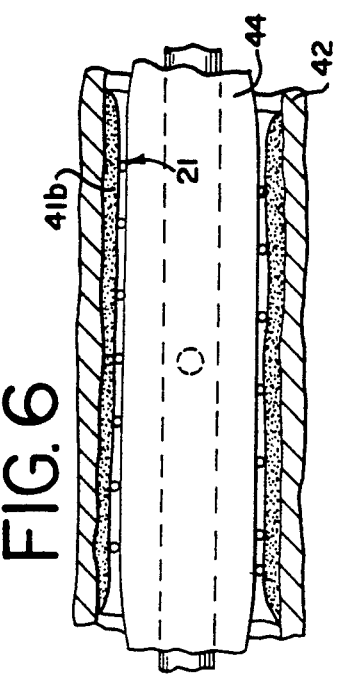

FIG. 11
FIG. 16
FIG. 17

WELDED RADIALLY EXPANDABLE ENDOPROSTHESIS AND THE LIKE

This application is a continuation of application Ser. No. 706,964, filed May 29, 1991, now abandoned.

BACKGROUND AND DESCRIPTION OF THE INVENTION

The present invention generally relates to endoprosthesis devices, to procedures for making them, and to the use thereof. More particularly, the invention relates to endoprostheses having a generally tubular shape and a generally helical construction that includes end turnings which are welded to adjacent turnings of the structure. Preferably, the welding procedure is carried out in an environment that promotes the formation of welds which are essentially crack-free and provide a welded attachment that is less susceptible to possible failure during operation of the endoprosthesis.

Endoprostheses incorporating the invention are radially expandable between a generally unexpanded insertion circumference and an expanded implantation circumference which is greater than the unexpanded insertion circumference. Included are a plurality of generally circumferential sections of the substantially helically shaped endoprosthesis, and at least some of these sections include one or more expandable segments that are bendable members which are generally collapsed when the endoprosthesis is in its generally expanded insertion orientation and which are generally opened when the endoprosthesis is in its expanded implantation orientation.

In general, endoprostheses are known for treating stenoses, stricture, aneurysm conditions, and the like. Endoprosthesis devices of this type, which are at times referred to as stents, are typically placed or implanted by a mechanical transluminal procedure. Often, these devices are percutaneously implanted within the vascular system to reinforce collapsing, partially occluded, weakened, or abnormally dilated localized sections of a blood vessel or the like. Stents of this type can also be used in the urinary tract, the bile ducts, the intestinal tract and the like. When endoprostheses or stents are used to treat a stenosis condition, typically this is done in association with a dilation element such as an angioplasty balloon. In this instance, the dilation element or balloon device opens the constriction, and the stent or the like is positioned thereat in order to prevent or at least substantially slow re-formation of the stenosis.

Various currently known stent products have structures that are essentially coiled springs. When this type of spring stent is tightly coiled, its diameter is reduced for insertion through a blood vessel or the like. When the coil is sprung or coiled more loosely, the stent assumes its expanded, implantation configuration. Maass et al U.S. Pat. No. 4,553,545 is illustrative of this type of coiled spring stent or endoprosthesis. Multi-helix or braided stents are also known. Stents of this general type suffer from poor maneuverability, and they are relatively thick walled and three-dimensional. They are also difficult to remove once implanted, and they may exhibit numerous exposed, relatively sharp or jagged ends. Palmaz U.S. Pat. No. 4,733,665 is representative of an expandable stent of this general type. Gianturco U.S. Pat. No. 4,580,568 illustrates a percutaneous endovascular stent formed of stainless steel wire that is arranged in a closed zig-zag pattern somewhat in the nature of a bookbinder spring. Such a structure is somewhat unsymmetrical, and it may be subject to reocclusion due to the very large open space that is typically present between the wires of this t e of device. Another type of stent is known as a Schatz stent, and it includes a hypodermic tube with longitudinal slots etched into its body. While such a device has a high ratio of unexpanded to expanded diameter, it is a comparatively rigid, sharp-edged device which is difficult to maneuver through a tortuous path and is not easily remove in a transluminal manner.

Wiktor U.S. Pat. No. 4,886,062 illustrates a generally helical endoprosthesis having a zig-zag pattern that can be expanded by an angioplasty balloon, the general helix shape having two free ends that present loose portions of the stent. In at least one other approach, means are provided for engaging free ends of a generally helically shaped endoprosthesis in order to avoid the presentation of loose ends.

With many of these currently developed or proposed stent structures, the axial length of the stent decreases as the circumference of the stent increases, which can be a disadvantage. For example, any such length reduction must be taken into consideration in selecting proper stent sizing for a particular implantation procedure. Also, this attribute of many prior stents requires the passage through the blood vessel or the like of a stent which is longer than the length actually needed for the implantation procedure being performed. This is a particularly difficult problem for procedures in which the stent must be passed through a pathway having twists or turns, especially for a stent structure that is not easily bendable. Other stents have design features which can decrease patency or which do not secure components together in a manner that reduces the possibility of cracking at securement locations.

The present invention avoids the various deficiencies of these types of prior art structures and provides important and advantageous features of endoprostheses or stents and the use thereof, including the following attributes which are believed to be important and advantageous for stents.

One important desirable attribute of the present stent is that it is radially compressible and expandable in a controllable manner. It provides a cylindrical supporting surface that remains free of portions which either project into the passageway defined within the cylinder or form an outward projection that could damage a vessel wall. The stent can easily pass through a blood vessel or the like when collapsed and expand to its implanted size in a substantially predictable manner after the stenosis, aneurysm or the like has been reached to provide a stent exhibiting excellent patency. It is constructed to minimize any possibility of damage to the vessel within which it is deployed.

Another desirable feature is that the stent is generally flexible throughout its length so that it is easily maneuverable through bends, branches and curves of the blood vessel or the like. The stent or endoprosthesis has a substantial amount of open space so as to allow for endothelialization along its length to minimize interference with collateral blood vessels and the like. The stent or endoprosthesis can be lodged securely into place at the desired location, while still being removable through a transluminal percutaneous procedure, should removal be needed.

In summary, the endoprosthesis of this invention includes a plurality of generally circumferential sections that are generally adjacent to one other along their respective opposing generally circumferential edges. At least one of these sections has an expandable segment that imparts radial expandability to the section. The expandable segment is an elbow-like member which is bendable between a generally collapsed or closed orientation and a generally opened orientation and is capable of assuming bending orientations between one that is fully closed and one that is fully opened. By this structure, the endoprosthesis or stent has an unexpanded insertion circumference and an expanded implantation circumference which is greater than the insertion circumference. The stent is made by a procedure that includes welding free ends to attach same to another portion of the stent, this preferably being carried out in a manner which minimizes cracking and possible subsequent welded attachment, while providing a stent that can be easily reduced in radial size and transluminally explanted if necessary.

It is a general object of the present invention to provide an improved radially expandable, axially extending endoprosthesis of enhanced patency and durability.

Another object of the present invention is to provide an improved endoprosthesis or stent that can be constructed to have very well-controlled radial expansion capabilities.

Another object of this invention is to provide an improved radially expandable axially extending endoprosthesis that is extremely maneuverable and capable of moving through a tortuous path.

Another object of the present invention is to provide an improved radially expandable axially extending endoprosthesis that can, if desired, be transluminally explanted by means of, for example, a snare lead or catheter device.

Another object of the present invention is to provide an improved radially expandable axially extending endoprosthesis which has no unattached free ends.

Another object of the present invention is to provide an improved axially extending endoprosthesis and procedure for securing otherwise free ends thereof to generally adjacent portions of the endoprosthesis.

Another object of this invention is to provide an improved procedure for making an axially extending and/or generally tubular endoprosthesis that is radially expandable and that has portions secured together.

Another object of the present invention is to provide an improved procedure and stent made thereby by which securement of an otherwise free end of a stent to another portion of the stent is carried out in a manner to minimize or virtually eliminate cracking at the attachment location.

Another object of the present invention is to provide an improved radially expandable endoprosthesis that substantially avoids the presentation of any unattached edges or ends which might damage a medical device balloon or otherwise present portions which project beyond the generally cylindrical sheath structure of the endoprosthesis.

These and other objects, features and advantages of this invention will be clearly understood through a consideration of the following detailed description.

BRIEF DESCRIPTION OF THE DRAWINGS

In the course of this description, reference will be made to the attached drawings, wherein:

FIG. 1 is an elevational view, partially broken away, of an endoprosthesis in accordance with the present invention;

FIG. 2 is an elevational view, partially broken away, of another embodiment of a stent according to this invention;

FIG. 3 is an elevational view of a stent together with a distal end of a balloon catheter;

FIG. 4 is a generally cross-sectional illustration of the endoprosthesis and catheter of FIG. 3 positioned within a blood vessel;

FIG. 5 is a generally cross-sectional illustration of an implantation stage subsequent to that shown in FIG. 4;

FIG. 6 is a generally cross-sectional illustration of an implantation stage subsequent to that shown in FIG. 5;

FIG. 7 is a generally cross-sectional illustration of an implanted endoprosthesis according to the present invention;

FIG. 8 is a perspective view of an apparatus suitable for use in carrying out the preferred welding procedure;

FIG. 9 is an elevational view of an unfinished endoprosthesis in accordance with this invention;

FIG. 10 is an enlarged partial view of one end of the unfinished endoprosthesis shown in FIG. 9;

FIG. 11 is a photomicrograph of an endoprosthesis having the weld feature in accordance with the present invention;

FIG. 16 is a photomicrograph of a welded joint of an endoprosthesis prepared according to the preferred procedure; and FIG. 17 is a photomicrograph of a cross-section of the FIG. 16 joint.

DESCRIPTION OF THE PARTICULAR EMBODIMENTS

Figure 12:
FIG. 12 and FIG. 13 are photomicrographs of welded joints of endoprostheses which were not prepared according to the preferred procedure.

A radially expandable axially extending endoprosthesis or stent is generally designated as 21 in FIG. 1. The stent includes a plurality of generally circumferential sections 22. In this illustrated embodiment, each of the circumferential sections 22 is formed from a single continuous, helically wrapped length, such as the illustrated undulating length of wire which is shown. At least one of these circumferential sections 22 includes at least one expandable segment 23.

Each expandable segment 23 is a bendable member that typically includes one or more legs 24. Each leg 24 is bendably secured to the rest of the circumferential section 22 by a so-called living joint or hinge that is a unitary or integral component joining two legs 24 together. In the illustrated embodiment, each leg 24 is bendably joined to another leg 24 through an integral member or hinge 25 having a generally arcuate shape. When the stent 21 expands, the integral member or hinge 25 permits opposing portions of the legs 24 to move farther apart, thereby increasing the circumference and diameter of the stent 21. Of course, the circumference and diameter of the stent 21 can be reduced by forces which move these legs 24 closer to each other.

The preferred manner of making the circumferential sections of the stent 21 includes first winding a strand of wire or other material generally tightly over a mandrel to the extent that the strand takes on the cross-sectional shape of the mandrel. Typically, this winding is done in a manner such that there is a substantial spacing between each individual wind of the strand. If desired, the strand can be subjected to a conventional annealing process for the type of wire material used.

Thereafter, the mandrel is removed, and the wound strand is subjected to flattening forces so that the three-dimensional wound strand is transformed into a generally planar or flattened length having undulating features or a generally zig-zag type of structure. In the preferred embodiment illustrated, this length has a generally sinusoidal character.

Next, this undulating length is wound, in a generally helical manner, around a substantially cylindrical mandrel. This generally helical wrapping procedure is continued until the desired number of circumferential sections 22 are formed to provide a stent body of a desired length. It may be preferable, depending upon the type of wire used, to heat anneal this helically wound structure. At this stage, the stent body has an overall structure such as that shown in FIG. 9 and FIG. 10. Each end portion preferably is generally bent backwardly on itself such that a tail portion 26 is provided as perhaps best seen in FIG. 10. When an extended free end such as the tail portion 26 shown in FIG. 10 is subjected to welding conditions as discussed in greater detail herein, the tail portion 26 is removed, and a weld such as that generally illustrated in FIG. 1 or FIG. 11, for example, results.

Weld 27 shown in FIG. 1 is in the nature of a butt weld in that leg portion 24 butts into the integral member or hinge 25, and the weld 27 is generally presented thereat. FIG. 2 illustrates a stent 21a having a slightly different weld which might be considered as a parallel weld 31 which is somewhat in the nature of a fillet weld wherein an extended leg portion 32 engages a portion of a leg 24 in a generally parallel manner at a weld 31. As illustrated in FIG. 1 and FIG. 2, the weld 27, 31 secures both free ends of the stent helix member to a portion of an adjacent circumferential section 24 of the helical body. In either event, the leg 24 is welded directly to the adjacent circumferential section in the absence of any needed additional mechanical feature, such as a portion of the free end formed into a loop, or otherwise bent generally back or onto itself or wrapped around another member. Instead, all that is required is a direct weld of a portion of the otherwise free end of the stent onto another portion of the stent.

The materials out of which stents according to the present invention can be made are preferably inelastic materials that can be generally characterized as malleable. Included are tantalum, titanium, silver, gold, annealed metals, and polymers to the extent that these materials can be welded together by appropriate welding techniques. The invention is especially advantageous and well-suited for endoprostheses made from tantalum wire. This is a material which is especially useful in preparing stents and the like because of its excellent biocompatibility properties; however, the attributes which provide these advantageous properties also complicate the welding procedure by making it more difficult to avoid cracking problems which occur when attempting to weld a material such as tantalum.

Stents of the general type illustrated herein are capable of moving through a typical tortuous path that may be encountered in vascular system implantation. The stents according to the present invention can be easily axially bent over a relatively small radius without damage or having to overcome a high bending resistance.

FIGS. 3 through 7 illustrate an implantation procedure for a stent 21 according to the present invention. A stenosis or lesion 41 within a blood vessel 42 is transluminally reached by a balloon catheter 43 having a stent 21 overlying the collapsed balloon 44 of the catheter 43. The balloon 44 is then expanded in a well-known manner, at which time the stent 21 is also expanded by opening the expandable segments thereof. An intermediate dilation position is shown in FIG. 5, and an initially dilated lesion 41a is shown therein. FIG. 6 shows additional dilation by the balloon 44, and the thus treated lesion 41b is also shown. After this stage is achieved, the balloon catheter 43 is removed, and the expanded stent 21 remains as generally shown in FIG. 7.

Stent 21 remains in place because the expanded material of the stent exerts a hoop stress when it is expanded to the size illustrated in FIG. 7 such that it will not collapse by inwardly directed radial forces presented by the treated lesion and vessel wall or the like. In other words, the hoop stress of the expanded stent is greater than the hoop forces exerted by the passageway within which the stent is implanted. In addition, the force required to open the collapsed stent by the balloon is less than the hoop force provided by the balloon, and the hoop stress of the collapsed or unextended stent is less than that of the hoop force provided by the pressurized balloon of the catheter. One feature that can contribute to the advantageous hoop stress properties of this stent is the ability of the stent to expand well beyond that needed to effect the dilation procedure.

Considering the apparatus illustrated in FIG. 8, this illustrates an approach that is particularly wellsuited for carrying out laser welding of tantalum stent terminations. Materials such as tantalum have a great affinity for oxygen, hydrogen and the like in that tantalum types of metals actively absorb gases such as oxygen. This is a feature which, for example, enhances the biocompatibility properties of these metals because a strong oxygen layer is formed on the surface of the metal. This advantageous property is a disadvantage when it comes to forming welds therein. When welding is carried out in the presence of even small amounts of oxygen or other gases having a strong affinity for tantalum or the like, an embrittlement is experienced. It is believed that the onset of such embrittlement conditions is especially likely during an operation such as laser welding wherein a metal is rapidly heated and quickly cooled thereafter.

An apparatus such as that illustrated in FIG. 8 will facilitate the formation of a laser weld in an environment that excludes gases such as oxygen for which tantalum or the like has a strong affinity. In theory, an ideal arrangement would be to provide a welding environment that has a very high vacuum, for example on the order of $10^{-4}$ Torr. It will be appreciated that this is an extremely low pressure, and it would be difficult and expensive to provide such an environment to carry out a welding operation, even one on an item as small as a stent. Rather than have to be concerned about the problems involved in an extremely low pressure operation, the arrangement in FIG. 8 provides an environment of inert gas such as argon, helium and other members of the inert gas family including those specified in the inert gas grouping of the periodic table.

The apparatus illustrated in FIG. 8 includes an enclosed welding compartment 51 having a removable cover 52 of glass or the like which will permit the laser beam to pass therethrough such as one originating from a YAG laser unit 53. A side stream of argon gas or the like from the laser unit passes through a nozzle 54 that is inserted through an opening 55, which is preferably sealed around the nozzle 54, into the compartment 51. The argon gas flow purges the compartment 51 of air which flows out of the top of the compartment 51, due in large measure to the fact that argon is heavier than air. After purging has been substantially completed, the flow of argon into the compartment 51 preferably is continued, but at a relatively low rate so as to maintain the argon environment within the compartment while preventing air from entering through small cracks or openings of the compartment, for example at locations where the cover 52 rests on support flanges around the top of the compartment 51.

A partially completed stent 56 is positioned on a stage 57, preferably having a grid pattern 58. Because of the extremely small size of the partially completed stent 56, a videocamera 59 and monitor 61 can be provided in order to assist in properly locating the laser beam for desired welding procedures. With the properly positioned laser beam, welding is accomplished to provide a weld 27 (FIG. 1), weld 31 (FIG. 2) or other desired weld by which a portion of the partially completed stent 56 is welded directly to an adjacent circumferential section. The laser beam is directed at an engagement location 62 of the type illustrated in FIG. 10. This effects the desired welding procedure wherein the tail portion 26 assists in the formation of the desired weld. An arrangement such as that shown in FIG. 10 would form a weld in the nature of butt weld 27 shown in FIG. 1. It has been found that, without the extra material such as the illustrated tail portion 26, it can often occur that the two portions do not actually weld to each other, but instead a welded ball type of structure is merely formed on an end of the terminal leg 24a. It has been found that the welds provided according to the invention have a tapering configuration wherein a gradual or feathered edge type of weld joins one of the legs with an adjacent turn or leg, a typical weld in this regard being shown in FIG. 11.

Upon closer examination, the type of weld illustrated in FIG. 11 is one that is substantially free of embrittlement and cracking which could lead to failure of the weld and the subsequent undesirable presentation of a free end of the stent. Such a free end would lead to possible damage to the dilatation balloon, such as the formation of a pinhole therein. The presence of even a single pinhole in the dilatation balloon will seriously hamper the operation of an angioplasty balloon or the like to the extent that it can be rendered inoperative and will not accurately deploy the stent and can interfere with subsequent removal of the catheter and balloon from the vessel or the like. Free ends can also have the potential for damage to the blood vessel wall and the like. Also, the welded arrangement which is characteristic of the present invention provides mechanical operation of the stent which is substantially lost when the weld either is not present initially or is lost due to weld weakening caused by lesions or cracks.

With more particular reference to the mechanical operation which is characteristic of the present stents, the weld fixes the unexpanded diameter of the end circumferential sections. Because of this, when the dilatation balloon radially expands the stent, the folded portions of the end sections are expanded in a controlled manner. Because both of the extreme end sections are tied in a generally circumferential manner, there will be an enhanced tendency of each integral hinge 25 to open in a generally uniform manner. This is not necessarily experienced when the ends are not welded in accordance with the present invention, particularly at the free end portion which, because it is not secured to the stent, it may simply lever outwardly rather than open at each hinge member to the extent desired or the extent that other hinge members 25 on the stent are opened in response to substantially the same degree of balloon expansion. Additionally, because the welded arrangement fixes the diameter of the end circumferential sections, the possibility of over-expansion is avoided, and the structural integrity of the end segments of the stent is assured, thereby enhancing the ability of the end segments to support the vessel wall.

The welding provides a closed loop that ensures a good starting point for expansion of each hinge member 25. Furthermore, this type of expansion is thereby favored over twisting of the coil by which the helix rotates somewhat along the lines of the coiled spring stents known heretofore. Coil twisting results in an expansion that is less controllable than that provided by the welded stent. A twisting movement can also lead to a "corkscrew" effect that imparts an undesirable cutting edge quality to the unwelded stent. The overall result of this invention is a stent that is more controllable so that it can be more uniformly placed over the deflated balloon and so that the surgeon can better predict the opening movement that will be imparted to the stent when the balloon is inflated.

Figure 13:
Figure 14:
FIG. 14 and FIG. 15 are photomicrographs of cross-sections of the joints of FIG. 12 and FIG. 13, respectively.
Figure 15:

Weld crack development can be experienced in welded tantalum stents even when an attempt is made to conduct the welding in the presence of an inert gas such as argon. FIG. 12 and FIG. 14 illustrate welds made by a YAG laser beam directed onto a partially completed stent 56 while a stream of argon gas is directed across the location at which the weld is being formed, but not within an apparatus of the type shown in FIG. 8. FIG. 13 and FIG. 15 respectively are photomicrographs prepared in conjunction with scanning electron microscopic examination of these welds after cross-sectioning. While the weld of FIG. 12 and FIG. 13 was able to withstand the sectioning procedure, cracks are evident. The weld of FIG. 14 and FIG. 15 was brittle, and the weld fell apart upon sectioning. FIGS. 12, 13, 14 and 15 reveal areas indicative of cracking in the heat affected or welded zones. In addition, the welds show various degrees of porosity, and no other obvious defects were evident.

The stent welds of FIG. 16 and FIG. 17 illustrate data generated upon scanning electron microscope examination of certain stents. Welds on both ends of each of three stents were formed with the assistance of the apparatus illustrated in FIG. 8. Each of the six welds revealed no significant evidence of cracking at the heat affected zone, that is at the weld area. Metallographic examination of all six welds showed no evidence of heat affected zone cracking as the result of welding. In addition, each of the welds revealed good fusion, and various degrees of porosity were noted within the weld bead as can be seen in the sectioned weld area of FIG. 17.

Generally speaking, welding can substantially reduce the tensile strength of a material such as tantalum. Tensile strength reduction will generally reduce the strength of the weld and contribute to weld failure. It has been found that when welding is carried out within an environment such as that provided in the FIG. 8 apparatus, the tensile strength at the weld typically is reduced when compared with that of raw tantalum wire which has not been subjected to heating indicative of welding, but the reduction in tensile strength is significantly less than that experienced when the welding is carried out under an argon stream only and without the benefit of the FIG. 8 type of apparatus.

It will be understood that the embodiments of the present invention which have been described are illustrative of some of the applications of the principles of the present invention. Numerous modifications may be made by those skilled in the art without departing from the true spirit and scope of the invention. For example, the welding procedures can use arc plasma techniques using, for example, inert gas such as argon.

I claim:

1. A radially expandable endoprosthesis, comprising:
   a plurality of generally circumferential sections, including end and intermediate generally circumferential sections, said end and intermediate generally circumferential sections being substantially adjacent to one another and generally parallel to each other in order to thereby substantially define an endoprosthesis having a longitudinal axis along which each of said generally circumferential sections are substantially axially spaced;
   each of said generally circumferential sections includes an expandable segment that imparts radial expandability to said generally circumferential section whereby said section has an unexpanded insertion circumference and an expanded implantation circumference which is greater than said unexpanded insertion circumference;
   said expandable segment of each generally circumferential section is a member that is bendable between a generally closed orientation and a generally opened orientation so as to impart radial expandability to the generally circumferential section;
   said generally circumferential sections form a continuous helix-like structure that defines an axially extending endoprosthesis, the helix-like structure having terminal portions of said end sections;
   each of said terminal portions of the end sections is welded to an adjacent one of said intermediate sections, thereby avoiding presentation of loose ends on the endoprosthesis, each of said welds directly securing the terminal portion to a bendable portion of the adjacent intermediate section, each of said welds has a generally tapering configuration having a feathered edge structure; and
   each said weld is a laser-formed weld made while the endoprosthesis is encased within an enclosed welding compartment filled with an inert gas and substantially free of oxygen, the laser-formed weld having been formed by directing a laser beam through a wall of the enclosed welding compartment, which wall retains inert gas within the enclosed welding compartment and permits the laser beam to pass therethrough to form the laser-formed weld;
   whereby the weld of the endoprosthesis exhibits substantial reduction of embrittlement and cracking, and the weld has significantly greater tensile strength, all when compared with an otherwise identical weld formed under a steam of the same inert gas and without the endoprosthesis being in the enclosed welding compartment.

2. The endoprosthesis according to claim 1, wherein said weld is a butt weld by which the terminal portion is generally perpendicular to the portion of the adjacent generally circumferential section to which it is welded.

3. The endoprosthesis according to claim 1, wherein said weld is a parallel weld by which the terminal portion is generally parallel to and closely engages the portion of the adjacent generally circumferential section to which it is welded.

4. The endoprosthesis according to claim 1, wherein said endoprosthesis is made of tantalum wire.

5. A method for making a radially expandable endoprosthesis, comprising the steps of:
   winding an elongated strand around a narrow wrapping surface of a mandrel so as to form a wound stand having a plurality of turns therein;
   subjecting the wound strand to flattening forces in order to form a generally flat undulating strand length;
   generally helically wrapping the undulating strand length around a mandrel in order to provide a plurality of generally circumferential sections forming a continuous helix-like structure having a plurality of generally circumferential sections including end and intermediate generally circumferential sections;
   welding a terminal portion of one of the generally circumferential end sections to an adjacent one of the intermediate generally circumferential sections, the welding step directly securing the terminal portion to the adjacent section to form a weld of generally tapering configuration having a feathered edge structure;
   carrying out the welding step within an environment of inert gas, and the welding step includes encasing the endoprosthesis within an enclosed welding compartment substantially free of oxygen and filled with an inert gas; and
   said welding step further includes directing a laser beam through a wall of the enclosed welding compartment, which wall retains inert gas within the welding compartment and permits the laser beam to pass therethrough, and to the area being welded to form a weld that exhibits substantial reduction of embrittlement and cracking and that has significantly greater tensile strength when compared with an otherwise identical weld formed under a stream of the same inert gas and without the endoprosthesis being in the enclosed welding compartment.

6. The method according to claim 5, wherein the inert gas atmosphere is argon gas.

7. The method according to claim 5, wherein the welding step includes providing a tail portion of the terminal portion which is present prior to welding and which does not remain as a tail portion upon completion of the welding step.

8. The method according to claim 5, wherein said winding step includes winding tantalum as the elongated strand, and said inert gas of the welding step is argon gas.

9. A radially expandable endoprosthesis made in accordance with a process comprising the steps of:
   winding an elongated strand around a narrow wrapping surface of a mandrel so as to form a wound strand having a plurality of turns therein;

subjecting the wound strand to flattening forces in order to form a generally flat undulating strand length;

generally helically wrapping the undulating strand length around a mandrel in order to provide a plurality of generally circumferential sections forming a continuous helixlike structure having a plurality of generally circumferential sections including end and intermediate generally circumferential sections;

welding a terminal portion of one of the generally circumferential end sections to an adjacent one of the intermediate generally circumferential sections, the welding step directly securing terminal portion to the adjacent section to form a weld of generally tapering configuration having a feathered edge structure;

carrying out the welding step within an environment of inert gas, and the welding step includes encasing the endoprosthesis within an enclosed welding compartment substantially free of oxygen and filled with an inert gas; and said welding step further includes directing a laser beam through a wall of the enclosed welding compartment, which wall retains inert gas within the welding compartment and permits the laser beam to pass therethrough and to the area being welded to form the weld;

whereby the weld of the endoprosthesis exhibits substantial reduction of embrittlement and cracking, and the weld has significantly greater tensile strength, all when compared with an otherwise identical weld formed under a stream of the same inert gas and without the endoprosthesis being in the enclosed welding compartment.

10. The endoprosthesis according to claim 9, wherein said winding step includes winding tantalum as the elongated strand.

11. The endoprosthesis according to claim 9, wherein the inert gas atmosphere is substantially argon gas and is free of oxygen.

12. The endoprosthesis according to claim 9, wherein the welding step includes providing a tail portion of the terminal portion which is present prior to welding and which does not remain as a tail portion upon completion of the welding step.

* * * * *

UNITED STATES PATENT AND TRADEMARK OFFICE
CERTIFICATE OF CORRECTION

PATENT NO. : 5,304,200
DATED : April 19, 1994
INVENTOR(S) : Ronald N. Spaulding

It is certified that error appears in the above-indentified patent and that said Letters Patent is hereby corrected as shown below:

On title page, item [56]
In the U.S. References Cited, No. 3,657,744, "Ersek" should read --Ersck--; No. 5,035,706, "Giantureo et al." should read --Gianturco et al.--.
Col. 2, line 4, "this t e" should read --this type--; line 10, "remove" should read --removed--.
Col. 3, line 1, "other" should read --another--.
Col. 9, line 68, "steam" should read --stream--.
Col. 10, line 18, "stand" should read --strand--.

Signed and Sealed this

Nineteenth Day of September, 1995

Attest:

BRUCE LEHMAN

Attesting Officer

Commissioner of Patents and Trademarks